United States Patent
Indla et al.

(10) Patent No.: US 9,955,890 B2
(45) Date of Patent: May 1, 2018

(54) HEART ELECTROPHYSIOLOGICAL SIGNAL ANALYSIS SYSTEM

(71) Applicant: Siemens Medical Solutions USA, Inc., Malvern, PA (US)

(72) Inventors: Vijaya Sarathi Indla, Bangalore (IN); Preetham Nagaraja Murthy, Bangalore (IN)

(73) Assignee: Siemens Healthcare GmbH, Erlangen (DE)

( * ) Notice: Subject to any disclaimer, the term of this patent is extended or adjusted under 35 U.S.C. 154(b) by 0 days. days.

(21) Appl. No.: 15/065,734

(22) Filed: Mar. 9, 2016

(65) Prior Publication Data

US 2016/0183832 A1 Jun. 30, 2016

Related U.S. Application Data

(62) Division of application No. 12/628,659, filed on Dec. 1, 2009, now Pat. No. 9,314,180.

(60) Provisional application No. 61/175,616, filed on May 5, 2009.

(51) Int. Cl.
*A61B 5/0456* (2006.01)
*A61B 5/0452* (2006.01)
*A61B 5/00* (2006.01)

(52) U.S. Cl.
CPC ............ *A61B 5/0452* (2013.01); *A61B 5/726* (2013.01)

(58) Field of Classification Search
CPC ...... A61B 5/0452; A61B 5/0472; A61B 5/726
See application file for complete search history.

(56) References Cited

U.S. PATENT DOCUMENTS

| | | | | |
|---|---|---|---|---|
| 2008/0319331 | A1* | 12/2008 | Zizzo | A61B 5/04012 600/511 |
| 2011/0040199 | A1* | 2/2011 | Hopenfeld | A61B 5/0452 600/515 |
| 2011/0040200 | A1* | 2/2011 | Douglas | A61B 5/0472 600/516 |

* cited by examiner

Primary Examiner — Michael D Abreu

(57) ABSTRACT

A system automatically detects and measures ST deviation of a heart wave ECG signal in the presence of noise and accommodates baseline variation of the signal and other artifacts. A system identifies a particular point in an electrophysiological signal representing heart electrical activity using an interface for receiving an electrical signal waveform comprising an R-wave and including an ST segment portion associated with heart electrical activity of a patient over a heart beat cycle. A signal processor processes data representing the electrical signal waveform by identifying an S point and T point in the electrical signal waveform and determining a first candidate J point in the electrical signal waveform having substantially a maximum distance from a line between the identified S and T points, the distance being measured perpendicularly to the line.

7 Claims, 8 Drawing Sheets

10

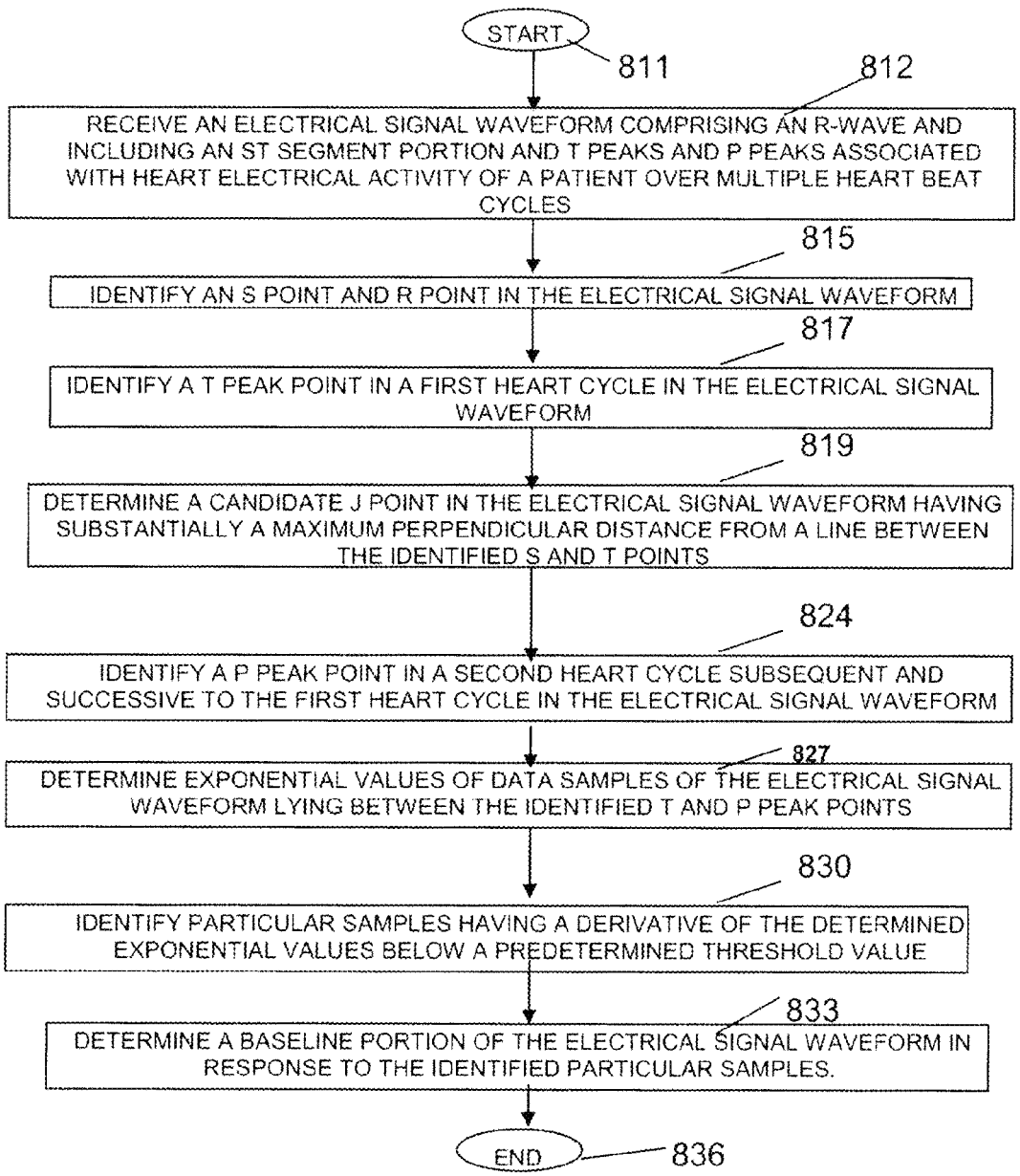

HEART ELECTROPHYSIOLOGICAL SIGNAL ANALYSIS SYSTEM

The present patent document is a divisional of application Ser. No. 12/628,659, filed Dec. 1, 2009, which is a non-provisional of Application Ser. No. 61/175,616, filed on May 5, 2009, the disclosure of which is hereby incorporated by reference.

FIELD OF THE INVENTION

This invention concerns a system for identifying particular points in an electrophysiological signal representing heart electrical activity, by determining and processing parameters of particular segments of the electrophysiological signal.

BACKGROUND OF THE INVENTION

An electrocardiogram (ECG) is used by cardiologists to aid in the diagnosis of various cardiac abnormalities. An ECG records heart electrical activity over a heart cycle as illustrated in FIG. 2 showing fiducial points and segments including ST, QRS and PQ segments. Fiducial points are landmarks in an ECG complex signal such as the isoelectric line (PQ junction), and onset of individual waves such as PQRST. Cardiac arrhythmia and ischemia are some of the conditions that are identified through the analysis of an ECG. There is a strong correlation between ST segment deviation and incidence of ischemia. Also ST deviation measurement is an important parameter in clinical study. Some known systems employ Wavelet Transforms for ECG signal examination involving Slope based analysis of a raw ECG signal. These systems are time consuming and have problems providing accurate results from noisy signals. A system according to invention principles provides automated ST deviation detection and addresses deficiencies and associated problems of known arrangements.

SUMMARY OF THE INVENTION

A system automatically detects and measures ST deviation of a heart wave ECG signal in the presence of noise and accommodates baseline variation of the signal and other artefacts. A system identifies a particular point in an electrophysiological signal representing heart electrical activity using an interface for receiving an electrical signal waveform comprising an R-wave and including an ST segment portion associated with heart electrical activity of a patient over a heart beat cycle. A signal processor processes data representing the electrical signal waveform by identifying an S point and T point in the electrical signal waveform and determining a first candidate J point in the electrical signal waveform having substantially a maximum distance from a line between the identified S and T points, the distance being measured perpendicularly to the line.

In a feature of the invention the signal processor determines exponential values of data samples of the electrical signal waveform lying between a T peak of a heart cycle and a P peak of a subsequent successive heart cycle. The signal processor identifies particular samples having a derivative of the determined exponential values below a predetermined threshold value and determines a baseline portion of the electrical signal waveform in response to the identified particular samples.

BRIEF DESCRIPTION OF THE DRAWING

FIG. 8 shows a flowchart of a process used by a system for identifying a particular point in an electrophysiological signal representing heart electrical activity, according to invention principles.

DETAILED DESCRIPTION OF THE INVENTION

Figure 1:
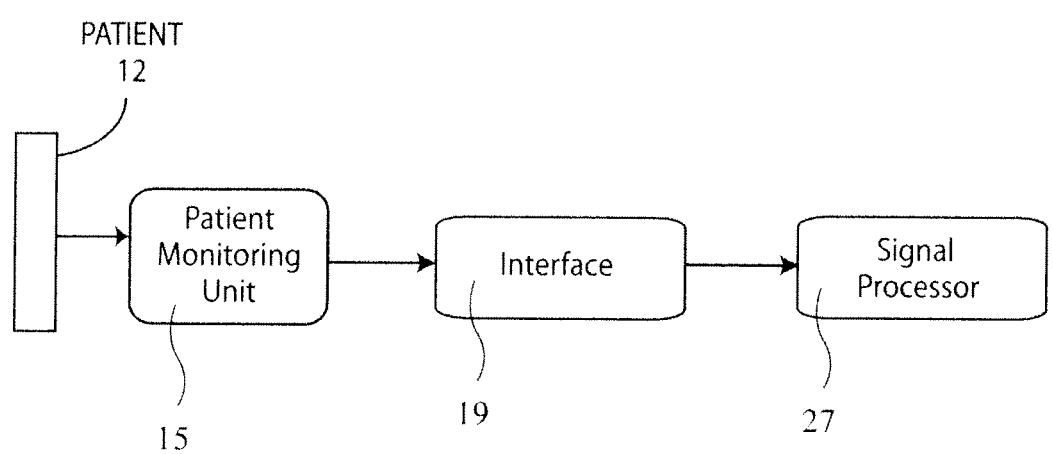
FIG. 1 shows a system for identifying a particular point in an electrophysiological signal representing heart electrical activity, according to invention principles.
Figure 2:
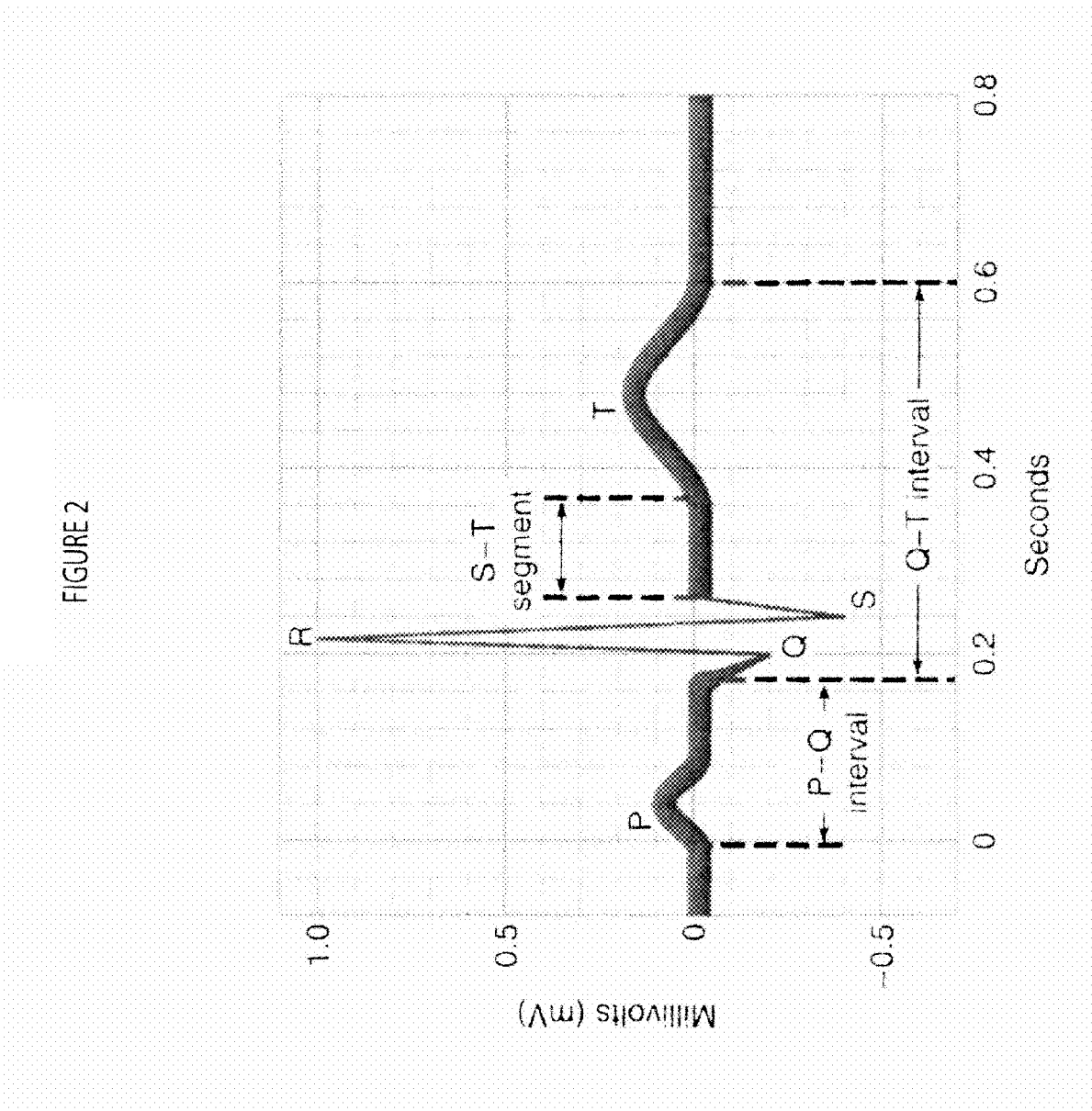
FIG. 2 shows fiducial points and segments of an ECG signal indicating heart electrical activity over a heart cycle.

A system automatically detects and measures ST deviation of a heart wave ECG signal in the presence of noise in the signal and accommodates baseline variation of the signal and other artefacts. FIG. 1 shows system 10 for identifying a particular point in an electrophysiological signal representing heart electrical activity. Patient monitoring unit 15 acquires signal data from patient 12 and processes the acquired data by buffering, filtering, amplification and digitization, for example, to provide an electrical signal waveform. Interface 19 receives the electrical signal (e.g., ECG) waveform from unit 15, comprising an R-wave and including an ST segment portion associated with heart electrical activity of a patient over a heart beat cycle. Interface 19 also pre processes the electrical signal to remove noise and baseline variation using signal filters. Signal processor 27 processes data representing the electrical signal waveform by identifying an R point using a peak detection function using one of multiple different known functions. Signal processor 27 processes data representing the electrical signal waveform by identifying an S point using a known Wavelet transform, for example and a T point in the electrical signal waveform. Signal processor 27 further determines a first candidate J point in the electrical signal waveform having substantially a maximum distance from a line between the identified S and T points, the distance being measured perpendicularly to the line. Signal processor 27 also computes a baseline of the electrical signal waveform.

Figure 3:
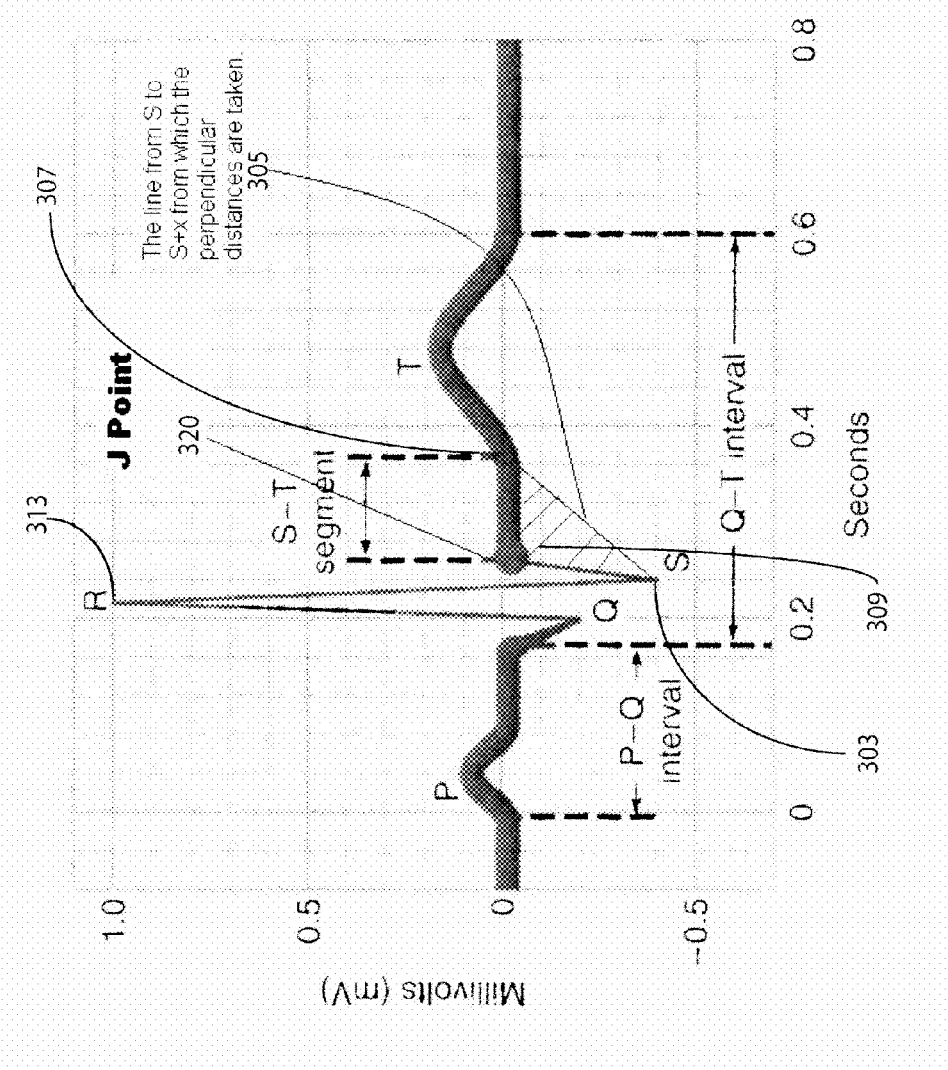
FIG. 3 shows an ECG signal indicating heart electrical activity over a heart cycle showing a J point when an S point is present, according to invention principles.
Figure 7:
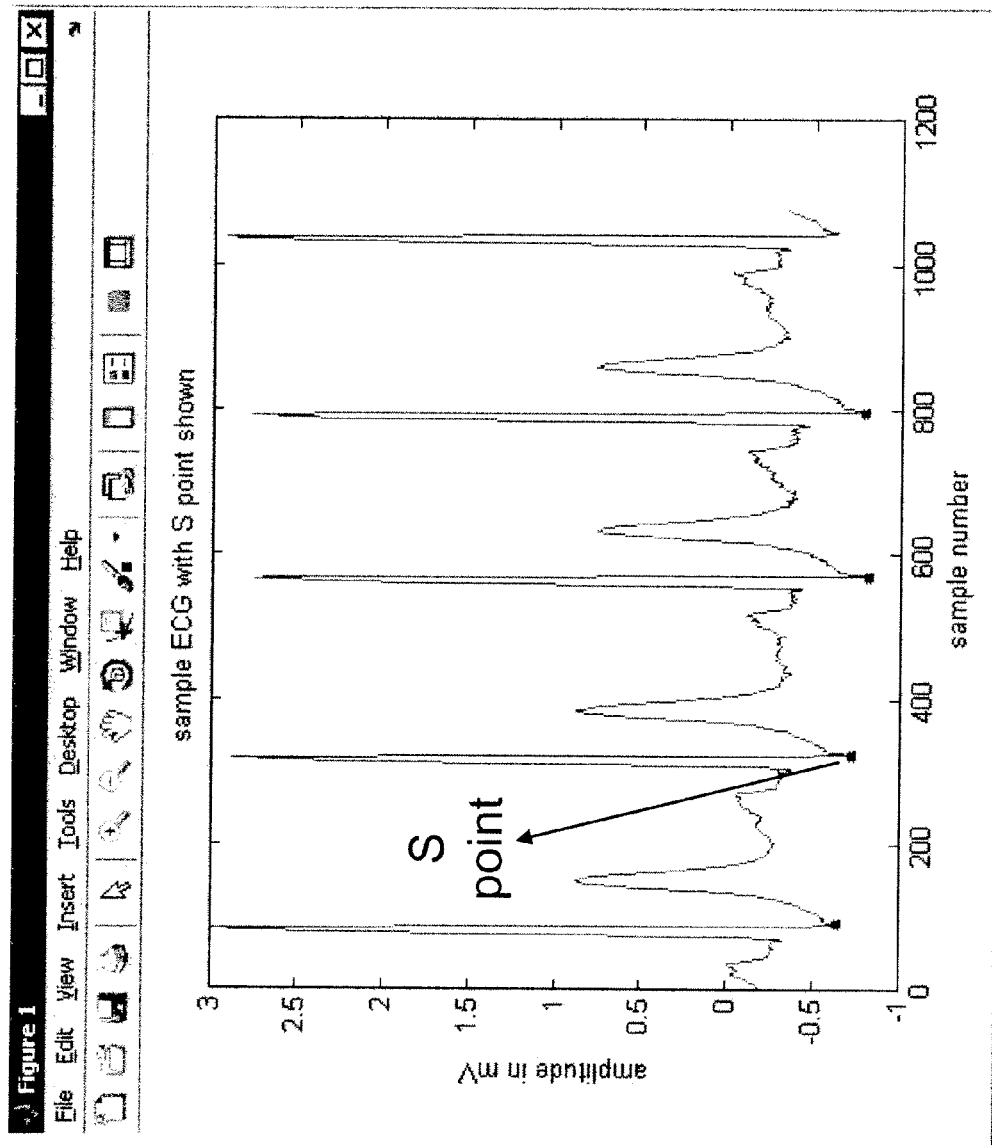
FIG. 7 illustrates S points in multiple heart cycles of an ECG signal, according to invention principles.

FIG. 3 shows an ECG signal indicating heart electrical activity over a heart cycle showing a J point when an S point is present and illustrating identification of a J Point using a Perpendicular Distance method. Signal processor 27 processes data representing the electrical signal waveform by searching for S point 303 of an ECG signal using a Wavelet transform, for example. An S point is a fiducial point in an ECG signal and comprises a first local minimum immediately following an R peak (visually it is the first negative peak after an R peak). Signal processor 27 determines whether the S point exists and its index if it does exist. An S point index is the temporal location of the occurrence of the S point. In a first signal processing iteration, signal processor 27 assumes the S point exists. If the S point exists, signal processor 27 projects a line L 305 from S point 303 to T point 307. FIG. 7 illustrates S points in multiple heart cycles of an ECG signal.

Figure 5:
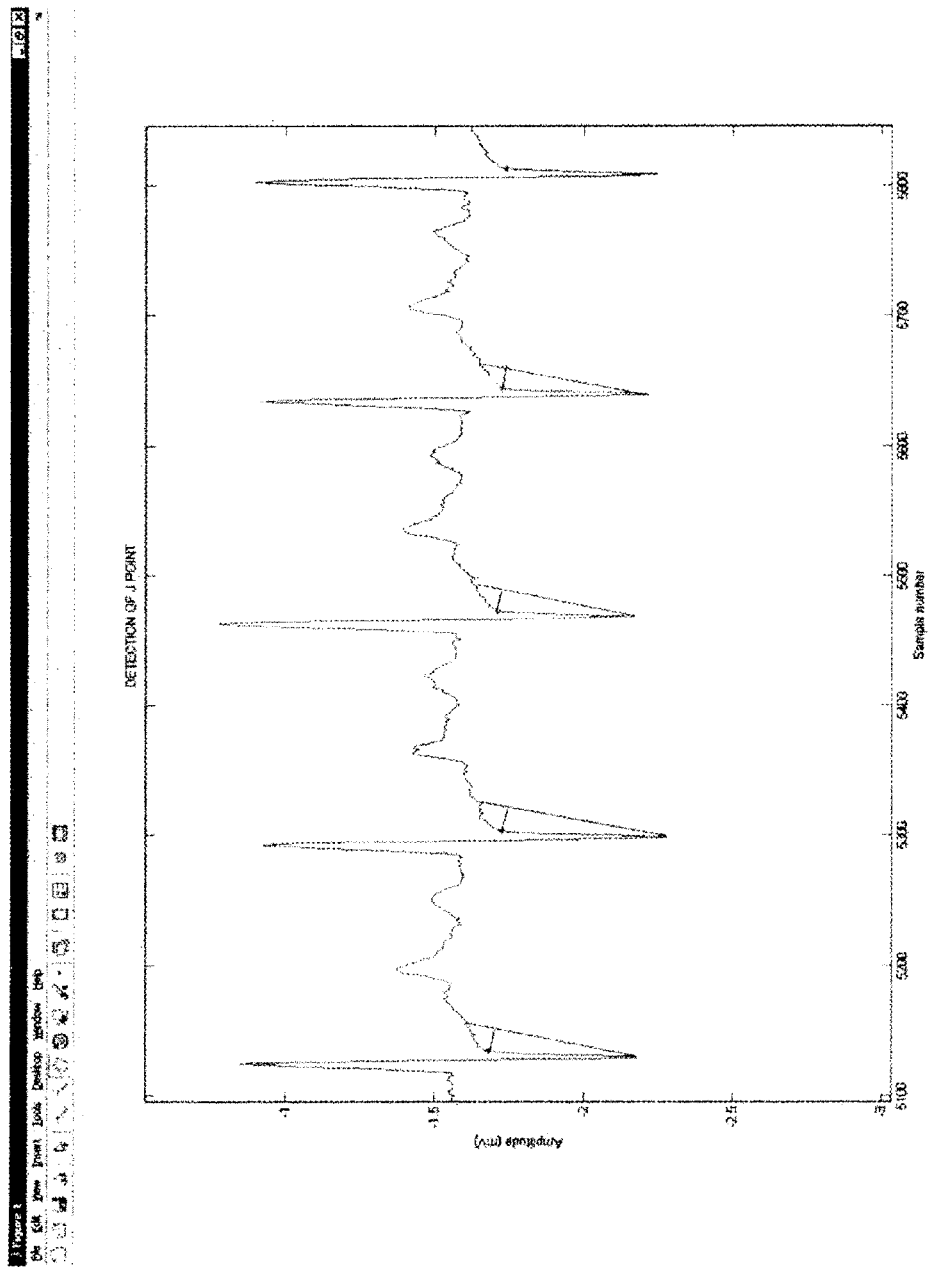
FIG. 5 similarly illustrates identification of a J point in multiple heart cycles of an ECG signal indicating heart electrical activity, according to invention principles.

Signal processor 27 detects a T point 307 by determining a highest point (or peak) of the ECG signal that lies between R+x and R+y values. Signal processor 27 takes this highest point as a T point 307 of that heart cycle. In this computation, R is the location of the R peak 313 for the heart cycle concerned, x and y are offsets in millisecond (ms) determined based on Heart Rate (HR). In this embodiment, for HR>120 beats per minute (bpm), x=60 ms and y=200 ms and for HR<=120 bpm, x=80 ms and y=300 ms. In this embodiment, the values for x and y are empirically determined but in another embodiment may be selected from predetermined data for a patient having similar demographic characteristics (including age, gender, height weight) derived from a population of patients. Signal processor 27 determines perpendicular distances, e.g. 309, from the signal enclosed between S 303 and T 307 to line L 305 as sample values and identifies and records a point in the ECG waveform having the largest perpendicular distance as J point 320. FIG. 5 similarly illustrates identification of a J point in multiple heart cycles of an ECG signal indicating heart electrical activity.

Figure 4:
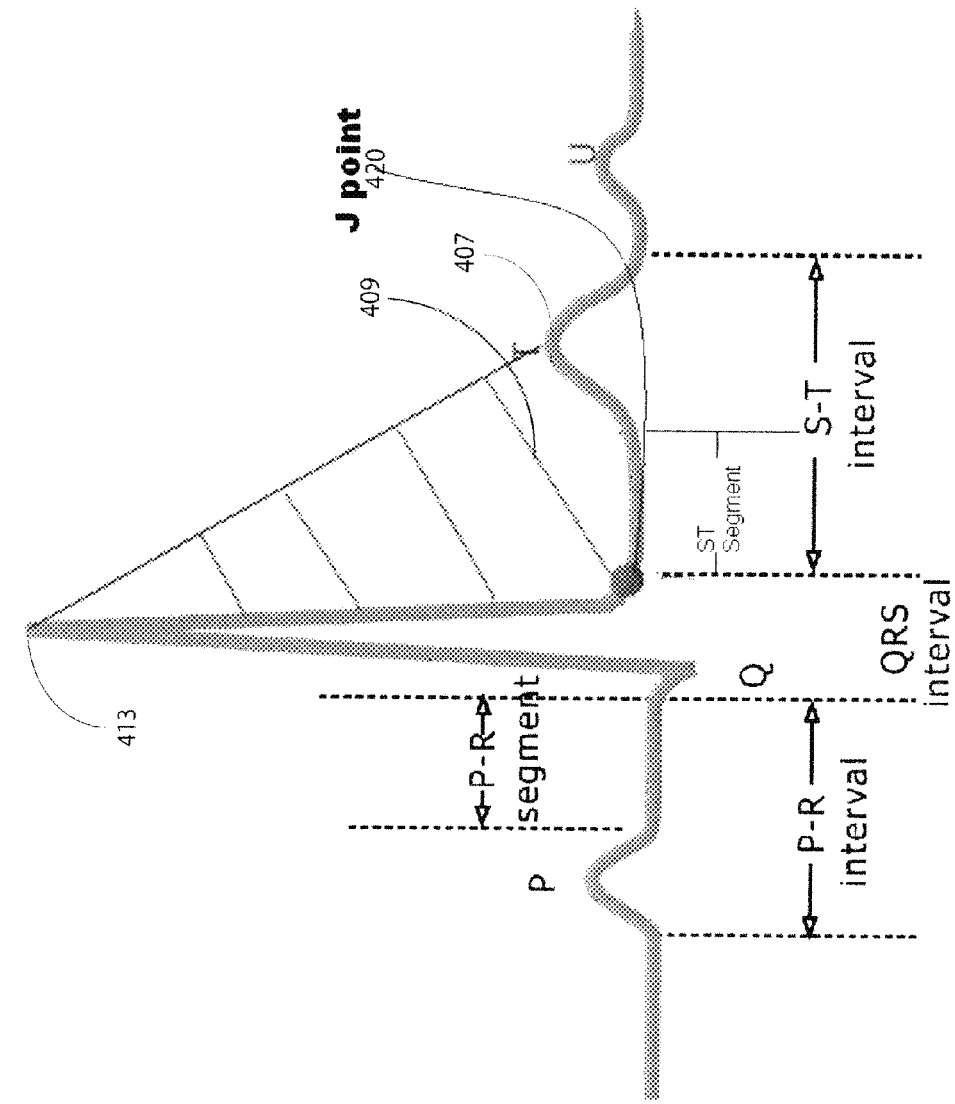
FIG. 4 shows an ECG signal indicating heart electrical activity over a heart cycle showing a J point when an S point is absent, according to invention principles.

Occasionally an S point may not be as distinct as is shown in FIG. 3. In such cases signal processor 27 does not detect an S point and proceeds with a workflow for an undetected S point. FIG. 4 shows an ECG signal indicating heart electrical activity over a heart cycle showing J point 420 when an S point is absent. In response to analyzing the ECG signal and determining the S point does not exist, signal processor 27 projects a line L from R point 413 to T point 407 and determines perpendicular distances, e.g., 409, from the signal enclosed between R and T to line L as sample values and identifies and records a point in the ECG waveform having the largest perpendicular distance as J point 420. Signal processor 27 improves accuracy of J point detection by performing processing of the ECG signal for J point detection using both the method for identifying a J point in the presence of an S point and the method for identifying a J point in the absence of an S point. Signal processor 27 determines a J point identified by either or both methods that lies closest to a time of 40 ms after an R peak and uses this as a J point.

The J point is often difficult to locate as it typically appears as just a small kink in an ECG signal. Owing to the presence of noise, which typically cannot be fully removed by filtering, there are many such kinks in the region of an expected J point making its detection difficult. Further, some signals may not have a prominent J point at all. In such cases, it is necessary to locate a point that best fits the possible location of a J point. The system addresses these problems using a location property of the J point as well the geometry of a neighbouring region. The system advantageously employs a temporal property of the J point (for example, the J point should occur at approximately 40 ms after an R peak) to improve the accuracy of the J point detection.

Figure 6:
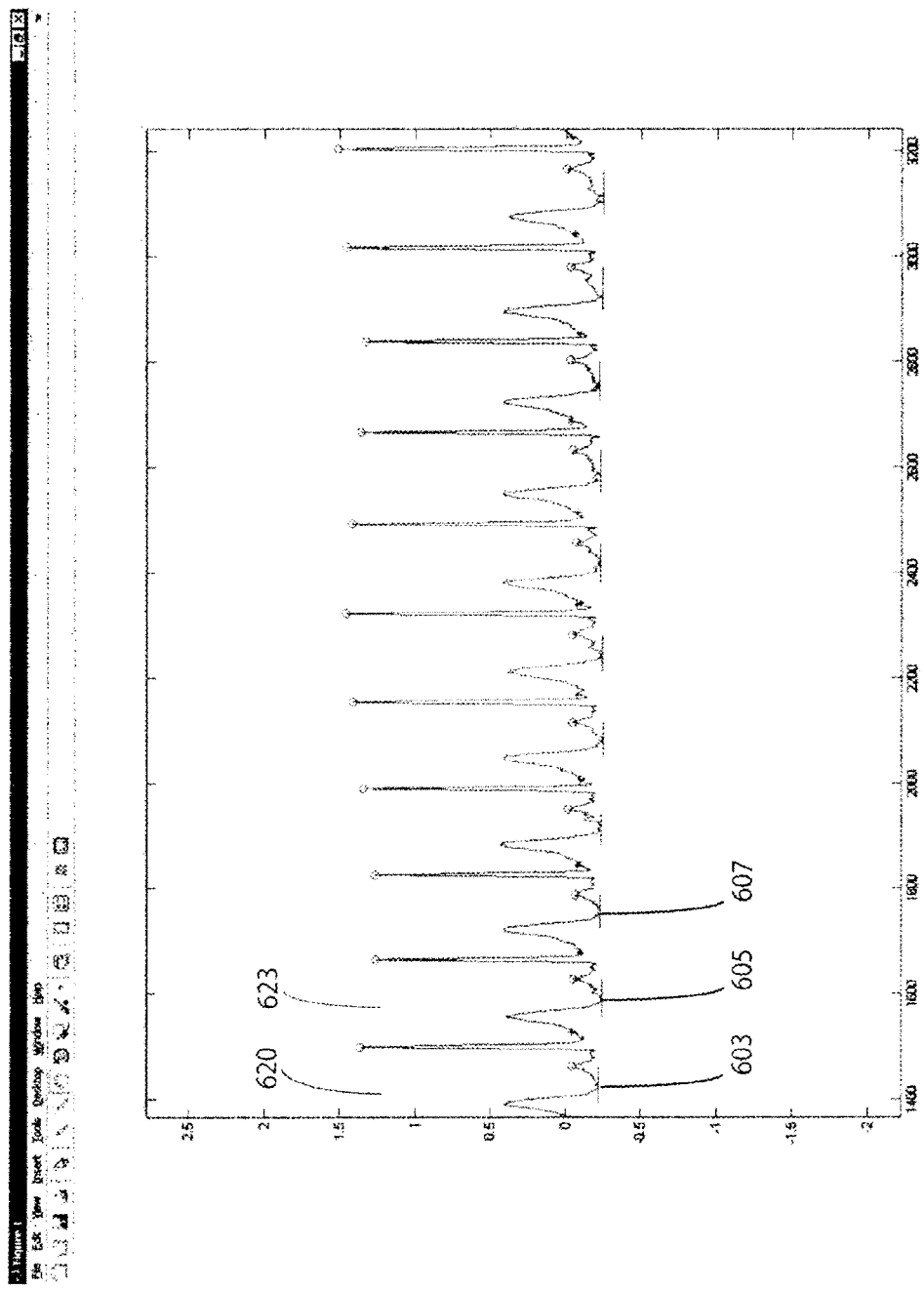
FIG. 6 illustrates computation of a baseline of an ECG signal indicating heart electrical activity over multiple heart cycles, according to invention principles.

FIG. 6 illustrates computation of a baseline of an ECG signal indicating heart electrical activity over multiple heart cycles. In computing baseline values 603, 605 and 607, for example, for individual heart cycles, signal processor 27 determines T and P peak values. Specifically, for an individual heart cycle 623, for example, signal processor 27 determines a T peak value of preceding heart cycle 620 and determines a P peak value of current cycle 623. Signal processor 27 determines a T peak value in the manner previously described in connection with FIG. 3. Signal processor 27 determines a P peak value by searching for a highest point (peak) of the ECG signal preceding an R peak between R−x and R−y values. In this computation, R is the location of the R peak for heart cycle 623, x and y are empirically determined offsets in millisecond (ms) determined based on Heart Rate (HR). In this embodiment, for HR<=120 beats per minute (bpm), x=80 ms and y=200 ms and for >120 bpm, x=60 ms and y=160 ms.

Further, signal processor 27 determines exponential values of ECG signal sample values between the determined T and P points. The region between the T and P points that qualifies as a baseline shows insignificant slope change and is difficult to detect. Thus signal processor 27 advantageously computes an exponential value of the samples values between the T and P points to exaggerate signal slope change. The exponential function creates a closer grouping of values for use in identifying a flattest segment of the signal. Processor 27 determines a derivative of the computed exponential values and determines a consecutive length of samples that have a derivative value (slope change) less than an empirically determined threshold (e.g., 0.05). Further, processor 27 determines a mode of the ECG signal values that belong to this consecutive length of signal as a baseline.

Signal processor 27 advantageously identifies a J point and computes an ECG signal baseline. Known systems typically determine a baseline by identifying the longest flattest segment between T and P peaks based on slope change. However, ECG signals (especially the region that qualifies to be the baseline) typically shows insignificant slope changes between neighbouring points. System 10 (FIG. 1) addresses these problems, by determining the exponential values of ECG signal values and by using the exponential values which exaggerate slope change between neighbouring points and make it easily observable.

FIG. 8 shows a flowchart of a process used by system 10 (FIG. 1) for identifying a particular point in an electrophysiological signal representing heart electrical activity. In step 812 following the start at step 811 interface 19 receives an electrical signal waveform comprising an R-wave and including an ST segment portion and T point and P point peaks associated with heart electrical activity of a patient over multiple heart beat cycles. In step 815 signal processor 27 processes data representing the electrical signal waveform by identifying an S point value and R point value in the electrical signal waveform and in step 817 identifies a T point peak value in a first heart cycle in the electrical signal waveform. In step 819 processor 27 determines a first candidate J point in the electrical signal waveform having substantially a maximum distance from a line between the identified S and T points, the distance being measured perpendicularly to the line. Processor 27 processes data representing the electrical signal waveform by determining a second candidate J point in the electrical signal waveform having substantially a maximum distance from a second line between the identified R and T points, the distance being measured perpendicularly to the second line. Processor 27 selects the closest of the first and second candidate J points to a point substantially 40 milliseconds after the R point. The selected J point is used for further analysis.

The determined J point identifies the start of an ST segment and processor 27 uses the identified J point in computing ST segment variation from the electrical signal waveform baseline and in response to the variation exceeding a predetermined threshold value, initiates generation of an alert message to a worker. Signal processor 27 determines J points for individual heart cycles of multiple sequential cycles and uses the identified J points in computing ST corresponding segment values for individual heart cycles of the multiple sequential cycles.

Processor 27 in step 824 identifies a P peak point of a second heart cycle subsequent and successive to the first heart cycle in the electrical signal waveform and in step 827 determines exponential values of data samples of the electrical signal waveform lying between the identified T and P peak points. In step 830, processor 27 identifies particular samples having a derivative of the determined exponential values below a predetermined threshold value and in step 833 determines a baseline portion of the electrical signal waveform in response to the identified particular samples. Specifically, processor 27 processes data representing the electrical signal waveform by determining a baseline portion of the electrical signal waveform as a portion having the largest number of consecutive identified particular samples. Also, processor 27 computes an ST segment value and variation of the ST segment value from the determined baseline portion of the electrical signal waveform and in response to the variation exceeding a predetermined threshold value, initiates generation of an alert message to a worker, indicating ischemia, for example. Processor 27 determines electrical signal waveform baseline values for individual heart cycles and computes ST segment variation from the electrical signal waveform baseline values for individual heart cycles. The process of FIG. 8 terminates at step 836.

A processor as used herein is a computer, processing device, logic array or other device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A display processor or generator is a known element comprising electronic circuitry or software or a combination of both for generating display images or portions thereof.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-8 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system automatically detects and measures ST segment deviation of a heart wave ECG signal, for example, from a baseline in the presence of noise in the signal and accommodates baseline variation of the signal between heart cycles and accommodates other artefacts. Further, the processes and applications may, in alternative embodiments, be located on one or more (e.g., distributed) processing devices on a network linking the units of FIG. 1. Any of the functions and steps provided in FIGS. 1-8 may be implemented in hardware, software or a combination of both.

What is claimed is:

1. A system for identifying a particular point in an electrophysiological signal representing heart electrical activity, comprising:
    an interface for receiving an electrical signal waveform comprising T peaks and P peaks associated with heart electrical activity of a patient over a plurality of heart beat cycles; and
    a signal processor for processing data representing said electrical signal waveform by
        (a) determining exponential values of data samples of said electrical signal waveform lying between a T peak of a heart cycle and a P peak of a subsequent successive heart cycle,
        (b) identifying particular samples having a derivative of the determined exponential values below a predetermined threshold value,
        (c) determining a baseline portion of said electrical signal waveform in response to the identified particular samples,
        (d) computing ST segment variation from the determined baseline portion of said electrical signal waveform, and (e) in response to the variation exceeding a predetermined threshold value, initiating generation of an alert message.

2. A system according to claim 1, wherein
said signal processor processes data representing said electrical signal waveform by
(i) identifying a T peak point in said electrical signal waveform and
(ii) identifying a P peak point in said electrical signal waveform.

3. A system according to claim 1, wherein
said signal processor determines the start of an ST segment by identifying a point in said electrical signal waveform having substantially a maximum distance from a line between S and T points, said distance being measured perpendicular to said line and
said signal processor uses the identified point in computing ST segment variation from said electrical signal waveform baseline and in response to the variation exceeding a predetermined threshold value, initiates generation of an alert message to a worker.

4. A system for identifying a particular point in an electrophysiological signal representing heart electrical activity, comprising:
an interface for receiving an electrical signal waveform comprising T peaks and P peaks associated with heart electrical activity of a patient over a plurality of heart beat cycles; and
a signal processor for processing data representing said electrical signal waveform by
(a) identifying a T peak point of a first heart cycle in said electrical signal waveform,
(b) identifying a P peak point of a second heart cycle subsequent and successive to said first heart cycle in said electrical signal waveform,
(c) determining exponential values of data samples of said electrical signal waveform lying between the identified T and P peak points,
(d) identifying particular samples having a derivative of the determined exponential values below a predetermined threshold value,
(e) determining a baseline portion of said electrical signal waveform in response to the identified particular samples,
(f) computing ST segment variation from the determined baseline portion of said electrical signal waveform, and
(g) in response to the variation exceeding a predetermined threshold value, initiating generation of an alert message.

5. A system according to claim 4, wherein
said signal processor processes data representing said electrical signal waveform by determining a baseline portion of said electrical signal waveform as a portion having the largest number of consecutive identified particular samples.

6. A system according to claim 4, wherein
said signal processor determines the start of an ST segment by identifying a point in said electrical signal waveform having substantially a maximum distance from a line between S and T points, said distance being measured perpendicularly to said line and
said signal processor uses the identified point in computing ST segment variation from said electrical signal waveform baseline and in response to the variation exceeding a predetermined threshold value, initiates generation of an alert message to a worker.

7. A system according to claim 4, wherein
said signal processor determines electrical signal waveform baseline values for individual heart cycles and computes ST segment variation from said electrical signal waveform baseline values for individual heart cycles.

* * * * *